US009321806B2

(12) United States Patent
Lo et al.

(10) Patent No.: US 9,321,806 B2
(45) Date of Patent: Apr. 26, 2016

(54) METHODS FOR RECOVERY OF LEAF PROTEINS

(75) Inventors: Martin Lo, Ashton, MD (US); Hong Fu, Fujian (CN)

(73) Assignee: University of Maryland, College Park, College Park, MD (US)

( * ) Notice: Subject to any disclaimer, the term of this patent is extended or adjusted under 35 U.S.C. 154(b) by 505 days.

(21) Appl. No.: 12/451,429

(22) PCT Filed: May 15, 2008

(86) PCT No.: PCT/US2008/006205
§ 371 (c)(1),
(2), (4) Date: Nov. 12, 2009

(87) PCT Pub. No.: WO2008/143914
PCT Pub. Date: Nov. 27, 2008

(65) Prior Publication Data
US 2010/0093054 A1    Apr. 15, 2010

Related U.S. Application Data

(60) Provisional application No. 60/938,267, filed on May 16, 2007.

(51) Int. Cl.
| C07K 1/36 | (2006.01) |
| C07K 1/14 | (2006.01) |
| C07K 1/30 | (2006.01) |
| A61K 36/81 | (2006.01) |

(52) U.S. Cl.
CPC . C07K 1/36 (2013.01); A61K 36/81 (2013.01); C07K 1/145 (2013.01); C07K 1/30 (2013.01)

(58) Field of Classification Search
None
See application file for complete search history.

(56) References Cited

U.S. PATENT DOCUMENTS

| 4,268,632 A | 5/1981 | Wildman | 435/232 |
| 4,289,147 A | 9/1981 | Wildman | 131/290 |
| 4,333,871 A | 6/1982 | DeJong | 530/379 |
| 4,334,024 A | 6/1982 | Johal | 435/232 |
| 4,340,676 A | 7/1982 | Bourque | 435/232 |
| 4,347,324 A * | 8/1982 | Wildman et al. | 435/232 |
| 4,400,471 A | 8/1983 | Johal | 434/232 |
| 4,588,691 A | 5/1986 | Johal | 530/379 |
| 4,666,855 A | 5/1987 | Yang | 436/89 |
| 5,369,023 A | 11/1994 | Nakatani | 435/193 |
| 6,028,250 A * | 2/2000 | Ohba et al. | 800/287 |
| 7,034,128 B2 | 4/2006 | Turpen | 530/417 |
| 2004/0102615 A1 | 5/2004 | Berna | 530/270 |
| 2006/0288449 A1 * | 12/2006 | Garger et al. | 800/280 |

FOREIGN PATENT DOCUMENTS

| EP | 0 235 697 | 9/1987 |
| WO | WO 03/063803 A1 | 8/2003 |
| WO | WO 2005/011657 A1 | 2/2004 |

OTHER PUBLICATIONS

Stastna et al. (Electrophoresis 2005, 26, 3586-3591).*
Hanson (Retrieved from the Internet: <<http://www.reeis.usda.gov/web/crisprojectpages/0207838-alternative-uses-for-tobacco-md.html>>, Published in 2006, Retrieved on Dec. 15, 2014).*
Supplementary European Search Report and opinion, issued in corresponding European patent application No. EP 08 75 4483, dated Aug. 9, 2010 (6 pages).
Servaites et al., "Diurnal Changes in Ribulose . . . ", Plant Science Letters, 35 (1984) pp. 115-121.
Dorion et al., "Cloning and characterization of a cytosolic isoform . . . ", Plant Science, 168 (2005) pp. 183-194.
Ginzel, K.H., (1992). Food from tobacco—A well-kept secret. Priorities: 4(1). http://www.acsh.org/healthissues/newsID.799/healthissue_detail.asp.
Pirie, N.W., "Leaf Protein and its by-products in human and animal nutrition." Cambridge University Press: Cambridge, U.K. pp. 15-16 (1987).
Pirie, N. W., "The Direct Use of Leaf Protein in Human Nutrition," Chem. & Ind. 61: 4-48, 1942.
Sheen, S. (1991). Comparison of chemical and functional properties of soluble leaf proteins from four plant species. J. Agile. Food Chem. 39: 681-685. http://www.oznet.ksu.edu/news/sty/2002/switchgrass_fuel070102.htm.
Tornatzky, L., Y. Batts, L. Casson, W. Loomis, and P. Waugaman (1996). Prospects for Plant-Based Biotechnology Products. The Southern Technology Council (STC).
Tso, T. C. (1990). Production, Physiology, and Biochemistry of Tobacco Plant, Ch. 22: Organic Metabolism—Tobacco Proteins. Ideals, Inc., Beltsville, MD.
Tso, T. C. (2006). Tobacco research and its relevance to science, medicine and industry. Contributions to Tobacco Research. 22: 133-146.
Wikipedia. Leaf Protein Concentrate. http://en.wikipedia.org/wiki/Leaf_protein_concentrate. (page last modified Sep. 9, 2009).
Wildman, S. (1983). An Alternate Use for Tobacco Agriculture: Proteins for Food Plus a Safer Smoking Material. http://www.wws.princeton.edu/cgi-bin/byteserv.prl/~ota/disk3/1983/8315/831507.PDF.
Bonner, P.L.R., 2007. Groundwork. In: Bonner, P.L.R., Protein purification. Taylor & Francis Group, New York, NY, pp. 26.
Bradford, M.M., 1976. A rapid and sensitive method for the quantitation of microgram quantities of protein utilizing the principle of protein dye binding. Anal. Biochem. 72, 248-254.
Degl'Innocenti, E., Guidi, L., Pardossi, A., Tognoni, F., 2005. Biochemical study of leaf browning in minimally processed leaves of lettuce (*Lactuca sativa* L. Var. *acephala*). J. Agric. Food Chem. 53, 9980-9984.

(Continued)

*Primary Examiner* — Suzanne M Noakes
*Assistant Examiner* — Jae W Lee
(74) *Attorney, Agent, or Firm* — Nash and Titus, LLC (57) ABSTRACT

A novel method for processing soluble plant leaf proteins is described. While leaf proteins are considered potentially the most abundant source of protein in nature, the lack of efficient processing techniques for leaf proteins has limited their commercial use. The method described in this patent provides a means of extracting and purifying leaf proteins from plants which is suitable for leaf protein production on an industrial scale.

18 Claims, 5 Drawing Sheets

(56) References Cited

OTHER PUBLICATIONS

Fantozzi, P., Sensidoni, A., 1983. Protein extraction from tobacco leaves: technological, nutritional and agronomical aspects. In Bodwell, C.E., Petit, L., Plant protein for human food. W.Junk Publishers., NewYork, NY, pp. 147-149.

Fennema, O.R., 1996. Water and ice. In: Fennema, O.R., Food Chemistry. Marcel Dekker, Inc. New York, NY, pp. 32-33.

Haschemeyer, R.H., 1973. Fractionation and analysis of proteins. In: Haschemeyer, R.H., Proteins: a guide to study by physical and chemical methods. John Wiley& Sons Inc, New York, NY, pp. 35.

Hatti-Kaul, R., Mattiasson, B., 2003. Release of protein from biological host. In: Hatti-Kaul, R., Mattiasson, B., Isolation and purification of proteins. Marcel Dekker, Inc. New York, NY, pp. 1.

Henningfield, J.E., Benowitz, N. L., Slade, J., Houston, T.P., 1998. Reducing the addictiveness of cigarettes. Tob. Control. 7, 281-293.

Kim, K., Portis Jr., A.R., 2006. Kinetic analysis of the low inactivation of Rubisco during catalysis : effects of temperature, O2 and Mg++. Photosynth. Res. 87, 195-204.

Komatsu, S., Masuda, T., Hirano, H., 1996. Rice gibberellin-binding phosphoprotein structurally related to ribulose-1,5-bisphosphate carboxylase/oxygenase activase. FEBS. Letters. 384, 167-171.

Kruger, N.J., 1994. The Bradford method for protein quantitation. In: Walker, J.M. (Ed.), Basic protein and peptide protocols. Humana Press Inc., Totowa, NJ, pp. 9-15.

Nelson, P.E., Surzycki S.J., 1976. A Mutant stain of chlamydomonas reinhardi exhibiting altered ribulosebisphosphate carboxylase. Eur. J.Biochem. 61, 465-474.

Platis, D., Labrou, N.E., 2006. Development of an aqueous two-phase partitioning system for fractionating therapeutic proteins from tobacco extract. J. Chrommatogy. A. 1128, 114-124.

Robinson, S.P., Streusand, V.J., Chatfield, J.M., Portis Jr., A.R., 1988. Purification and assay of Rubisco Activase from leaves. Plant. Physiol. 88, 1008-1014.

Salvucci, M., Anderson, J., 1987. Factors affecting the activation state and the level of total activity of Ribulose bisphosphate carboxylase in tobacco protoplasts. Plant. Physiol. 85, 66-71.

Scopes, R.K., 1987. Making an extract. In: Scopes, R.K., Protein purification principles and practice. Springer Verlag New York Inc, New York, NY, pp. 26.

Simpson, R.J., 2004. Preparing proteins for proteomic analysis. In: Simpson, R.J., Purifying proteins for proteomics: a laboratory manual. Cold Harbor Laboratory Press, New York, NY, pp. 17.

Tso, T.C., Kung, S.D., 1983. Soluble proteins in tobacco and their potential use. In: Telek, L.; Graham, H.D.; Leaf protein concentrates. AVI Publishing Company, Inc. Westport, CT, pp. 117-129.

Tso, T.C., 1990. Organic metabolism tobacco proteins. In Tso, T.C., Production, physiology, and biochemistry of tobacco plant. Ideals Inc., Beltsville, MD, pp. 487.

\* cited by examiner

METHODS FOR RECOVERY OF LEAF PROTEINS

PRIORITY INFORMATION

This application claims priority from the provisional application Ser. No. 60/938267 which was filed May 16, 2007, and PCT application PCT/US2008/006205, filed May 15, 2008, the entire contents of both of which are incorporated herein by reference.

GOVERNMENT INTERESTS

This invention was made with U.S. government support under USDA-CSREES Award No. 2006-34467-17102. The government has certain rights in the invention.

FIELD OF THE INVENTION

The invention of this application relates to novel methods for obtaining proteins from plant leaves for use in food and industrial products.

BACKGROUND OF THE INVENTION

Leaf proteins are potentially the cheapest and most abundant source of protein in the world (Wikipedia, 2008a, Pirie, 1987). (Full reference citations of these and all references mentioned herein are included at the end of the specification.) They are also highly nutritious and have many desirable functional characteristics which could make them useful in both food and industrial products.

The term "leaf protein" as used in this invention disclosure is intended to refer to all water-soluble proteins contained in plant leaves. It is well known that soluble leaf proteins are found in all known chlorophyll-containing plants. The present invention pertains specifically to soluble leaf proteins.

Approximately half of the soluble protein in plant leaves is made up of "rubisco" (ribulose-1,5-bisphosphate (RUBP) carboxylase/oxygenase or "RuBisCO") (Johal, 1982). Rubisco, which is found in all known green plants, appears to be the most abundant leaf protein, and it may be the most abundant protein on earth (Wikipedia, 2008b). Rubisco is the enzyme which catalyzes both the carboxylation and oxygenation of RUBP in plants, i.e., the key reactions in photosynthesis and photorespiration (Tso, 1990). Rubisco is the primary component of "fraction-1 protein," a term developed by Wildman (1983) to refer to the portion of the soluble leaf protein which can be crystallized out during leaf protein processing.

Rubisco has nutritional value comparable to casein, the milk protein (Wildman, 1983). Studies have shown that rubisco has a significantly higher Protein Efficiency Ratio (PER, i.e., weight gained/protein consumed) than either casein or egg protein (Tso, 2006). Tornatzky (et al., 1996) reported that rubisco appears suitable for kidney dialysis patients and other persons whose bodies do not produce adequate protein, due in part to the fact that rubisco crystals can be washed clean of salts (Tornatzky et al., 1996).

Rubisco also has excellent binding, gelling, foaming, whipping and emulsifying characteristics (Wildman, 1983; Sheen 1991). In addition, rubisco is colorless, tasteless and odorless, which makes it attractive for incorporation into food or industrial products. (Wildman, 1983). Rubisco is relatively stable and can be shipped in crystalline form or produced in a powder (Tornatzky et al., 1996). Given these desirable nutritional and functional properties, rubisco may prove suitable for incorporation into a range of both food and non-food products for such purposes as a nutritional supplement, binding agent or emulsifier. In fact, Wildman (1983) wrote that the functional properties of rubisco are similar to egg albumin or casein.

The remaining half of soluble leaf proteins do not crystallize as readily as fraction-1 proteins. They are sometimes referred to as "fraction-2" proteins (Wildman, 1983), but a term used to describe those soluble proteins which do not crystallize during leaf protein processing. These proteins share, however, many of the same beneficial traits as rubisco. They have a PER and nutritional quality comparable with casein (Tso, 2006; Wildman, 1983). Like rubisco, they are colorless and tasteless (Tso, 2006). They are also water-soluble (Wildman, 1983). With appropriate extraction methods, fraction-2 proteins could demonstrate the same functional properties as rubisco and have the same commercial applications (Wildman, 1983). Both the so-called "fraction-1" and "fraction-2" proteins are pigment-bound proteins.

Potential yields of leaf proteins are very large. Wildman (1983) reported yields of 6% of total plant solid dry matter as leaf proteins in tobacco. In our own field trials using tobacco as a source of leaf protein, we have obtained crude protein yields of approximately 13% of total leaf dry weight from tobacco variety MD 609 LA, a variety of Maryland tobacco which contains low alkaloids. Our average annual biomass yields exceed six dry tons per acre, when we cultivate tobacco for leaf protein recovery. Since the leaves represent about half of this total biomass, our projected leaf protein yields are approximately 800 pounds/acre.

Pirie may have been the first to seriously propose the use of leaf proteins as a source of nutrition, during the 1940's (Pirie, 1942, 1987). However, the protein extraction methods developed by Pirie resulted in green protein preparations which had odor, taste and texture which rendered them undesirable for human consumption (presumably due to inadequate removal of chlorophylls) (Wildman, 1983).

During the 1970's researchers at the USDA Western Regional Research Center modified and improved the technology developed by Pirie to produce a leaf protein concentrate from alfalfa which they called "Pro-Xan." In the later versions of this process, soluble proteins were coagulated by heat to produce a bland, off-white material containing 90% protein (Wildman, 1983). Wildman (1983) reported that the rubisco in this resulting protein was denatured together with the fraction-2 protein, and that it lost its functional characteristics.

In the early 1980's Wildman (1983) and Wildman and Kwanyuen (1981) developed a technology for extracting rubisco from tobacco leaves which relied on application of sodium metabisulfite. The aerial portions of freshly harvested tobacco plants were sprayed with a 0.5 percent solution of sodium metabisulfite as they fell into a pulping device. The pulp was placed into a screwpress which led to a recovery of a "green juice" containing the soluble proteins. This green juice was pumped into a heat exchanger which rapidly heated the juice to about 125° F. The juice was then rapidly cooled to room temperature. Wildman wrote that this abrupt temperature change aided in particulate matter aggregation to which green pigments and other lipoidal compounds are attached. The green juice then entered a continuous flow centrifuge which removed the starch and 85% of the green particulate material. A partially clarified brown containing the soluble proteins juice emerged from the centrifuge. The partially clarified brown juice was then pumped to a rotary vacuum filter which removed the last traces of green sludge. The clear brown juice emerging from the filter was then sent to a storage tank, where crystallization of the rubisco protein began within 3-6 hours of storage and was completed within 3-4 hours after crystallization began. Wildman reported that he added acid to the mother liquid at pH 4 in order to precipitate the fraction-2 proteins, while noting that this was not a desirable method because it resulted in denaturation of the proteins.

Bourque (1982) developed a method for the crystallization of rubisco which involved mixing a fraction-1 protein solution with a precipitant solution with a pH generally in the range of 4.8-7.2, to produce a mixed solution of protein solution mixed with precipitant solution having a final pH in the range of pH 6.6-7.0, which lead to crystallization of the fraction-1 protein.

Bourque mentioned that the protein solution could be obtained by standard fraction-1 plant protein purification processes previously described in the literature. For example, he wrote that it is possible to homogenize the leaves in a high salt (i.e., 1.0 M NaCl) buffer, filter the homogenate to remove larger solids, and then centrifuge to obtain a supernatant containing soluble protein, and exchanging a low salt buffer (i.e., 0.2 M NaCl) for the high salt buffer, and then eluting the protein solution from a column with the low salt buffer, and then precipitating the protein by adding a precipitant such as ammonium sulfate to provide 30-50% precipitant saturation. The resulting precipitate could then be crystallized using the technique disclosed by Bourque. Bourque reported that his invention was suitable for use with fresh leaves from tobacco, corn, potato, tomato or alfalfa.

Johal (1982, 1983 and 1986) developed a technique for the crystallization of rubisco to over 90% purity. In this technique, the leaves would first be homogenized in a buffer solution containing tris-HCL or phosphate or borate, at concentrations of 0.05M to 0.2M. The buffer solution would have a pH range of 7.8 to 8.25, with the optimal pH around 8.2. Polyethylene glycol would be added to represent up to 15% of the solution. The supernatant would be refrigerated at about 4° C. Johal (1982) reported that adding magnesium chloride would increase crystal yield. Johal reported that his technique had proven successful using several species, including tobacco, alfalfa, ryegrass, tomato and spinach.

DeJong (1982) reported a coagulation method for preparing leaf protein concentrates. Physically macerated leaves were subject to a cross-linking reagent such as gluterahldehyde, and then treated with potassium bisulfate to lower the pH to between 3 and 5. This treatment would precipitate soluble protein from the green juice, and then coagulate suspended proteins, resulting in the separation of a leaf protein concentrate.

SUMMARY OF THE INVENTION

As noted above plant leaf proteins have many reported uses. They have a nutritional value comparable to milk or soy protein. They have excellent binding, emulsifying, gelling and foaming characteristics. They are also odorless and tasteless, which make them suitable for incorporation into a range of industrial and food products. However, the lack of available processing technologies for extracting or purifying leaf proteins has limited their commercial use.

Many prior efforts to recover leaf proteins have involved many steps and not proven scalable. In particular, much of the prior art has focused on causing leaf proteins to crystallize out of solution. The inventors here have discovered a process that essentially inverts this approach. Rather than attempting to remove the protein, our process focuses on keeping the proteins in a solution so that we can remove the different non-proteins. Once the non-protein materials are removed, we can then dry down the proteins into a usable form. Our method minimizes the number of steps, and is thereby scalable to an industrial level.

This invention relates to a novel and scalable method for recovering soluble leaf proteins from plants. One novel aspect of our method involves the immediate solubilization of leaf proteins in a buffer solution at the time that plant cell walls are initially disrupted. The proteins are kept solubilized throughout the extraction process, which permits us to remove non-protein components of the leaves, such as cellulosic materials and chloroplasts, without losing or denaturing the proteins. Once these non-protein components are removed, we then dry down the proteins. This results in a soluble protein powder which is stable, easy to store, transport and use for commercial applications.

Also unlike many embodiments of the prior art, our method avoids the application of heat treatments. Application of heat, while it can help to separate the proteins, can also lead to protein denaturation. The method we have developed avoids denaturation and loss of protein functionality.

The inventors experimented with their novel method extensively using tobacco plants, specifically *Nicotiana tabacum*. However, as would be understood by someone having skill in this art, the principles and procedures which proved effective in recovering leaf proteins from tobacco would be applicable to other chlorophyll-containing plant species. Therefore, other *Nicotiana* species are well within the scope of this invention, as are of course other plants that contain chlorophyll and leaf proteins. This includes plant species that might not be expected to produce high yields of protein—certainly those that do produce high yields are excellent candidates for our methods. Examples of plants that would be especially useful in our methods include alfalfa, ryegrass, tomato, spinach, or potato, either because they are related to tobacco or because they are known to have high concentrations of leaf proteins.

In its broadest embodiment, the method contemplates recovering leaf proteins from plant leaves, and comprises the following steps. First, the cell walls of plant leaves containing leaf proteins are disrupted so that soluble leaf protein is exposed. Disruption of the cell walls can be carried out by any known methods as long as no heat treatment is applied, or any other treatment which would cause denaturation of the proteins. For instance, known and effective cell wall disruption methods include chopping, grinding or crushing the leaves by hand or mechanically, maceration procedures, pulping, mechanical pressure, using rollers, homogenizing, and the like. It is very important that the cell disruption take place under five conditions: (1) a temperature between about 0°-about 25° Celsius which is maintained throughout the protein recovery process; (2) substantially simultaneous application of a buffer solution to the soluble leaf proteins as they are being exposed during cell wall disruption, which is intended to solubilize the exposed leaf proteins as quickly as possible (e.g., cell disruption occurs in the presence of the buffer solution); (3) a buffer solution having a pH level which is within two pH units of the pH of the plant leaf "juice" (liquid exposed from cell wall disruption, including both leaf proteins and other leaf material) but at least one entire pH unit away from the isoelectric point (pI) of the soluble leaf proteins; (4) a buffer solution having a buffering region that is effective within the pH level of (3) above; and (5) a ratio of buffer solution to leaves which is greater than 1:1 (w/w) and preferably is sufficiently high to assure that substantially all disrupted leaf material comes into contact with the buffer solution (so as to maximize protein yield).

A novel and important feature of our method is that we solubilize the leaf proteins in a buffer solution at the time of the initial cell disruption, and then keep them in solution while we sequentially pull out the non-protein materials. Keeping the proteins in solution substantially simplifies the process of removing the non-protein materials. Once the non-protein components are removed, the protein-containing solution can be dried down to form a protein powder which is soluble, stable and easy to use or transport. This process results in a high yield of protein, while minimizing protein denaturation.

Throughout the various steps of our method to recover leaf proteins, it is preferable to keep the temperature between about 0°-about 25° Celsius. Temperatures above 25° Celsius would cause denaturation of the proteins, and dramatically decrease final yield. This is another one of the novel features of our method, and one reason why it is so effective at producing a good yield of protein.

The buffer solution should contact the plant leaves substantially simultaneously with cell wall disruption, so as to contact the exposed leaf proteins as soon as possible. This maximizes the buffering and stabilizing effect of the solution, so that the desired leaf proteins stay soluble. The buffer solution must include a buffer system suitable for protein extraction. Buffer solutions by definition function by resisting changes in pH following the addition of small quantities of acids or bases. Buffer solutions are effective within their buffering regions, that is, the amount of protons or hydroxide ions the buffer can absorb without a significant change in pH. Within its buffering region, a buffering solution is effective as a buffer—that is, will have a pH that does not fluctuate significantly. The minimum requirements for the buffer system in our invention are that it is able to solubilize leaf proteins at their acceptable, and preferably optimal, pH (for solubility) within its buffering region, and have a pH as close as possible to the pH of the liquid leaf material (within two pH units) while simultaneously remaining at least one pH unit or whole number away from the isoelectric point from the leaf protein material. (In other words, if the plant liquid resulting from leaf disruption had a pH of 6.5 and the leaf protein had an isoelectric point of 5.8, the possible pH range of the buffer solution would be between pH 6.8 and 8.5 (with the precise value to be determined by the testing described immediately below). This is because pH 6.8 would be the closest pH to the pH of the leaf material which satisfied the minimum threshold of remaining a full pH unit away from the isoelectric point, while pH 8.5 would be the maximum of two pH units away from the pH of the plant leaf material.

The technology described in this invention would be usable by any person reasonably skilled in the art to produce a relatively pure leaf protein powder from tobacco or other *Nicotiana* species, species related to tobacco such as tomato or potato, or species with a high concentration of leaf proteins such as alfalfa or spinach. As would be understood by someone having ordinary skill in this art, this is not an exhaustive list of plant types and species. Although specific parameters (i.e., optimal pH level, etc.) might vary between species, the steps of the methods would remain the same.

Using any plant leaf containing chlorophyll and soluble leaf proteins, the initial step would be to disrupt the plant cells using any of the well-known cell disruption processes described above to expose the leaf proteins. Substantially simultaneously with this disruption, the buffer solution would be applied. The specific parameters of the buffer solution would be determined as follows.

Determine pH of the liquid juice in the plant leaf which is exposed following cell disruption, using any standard technique for determining pH. The pH of the buffer solution should be no more than two pH units from the pH of the plant leaf material, to keep the plant protein close to natural conditions and maximize solubility. (In other words, if the pH of the exposed liquid leaf material were 7, then subject to the variables below, the range of possible pH values for the buffer solution would be from pH 5 to pH 9).

Determine the isoelectric point (pI) of the leaf protein of the plant of interest. As is well known, the isoelectric point is the pH at which a molecule or surface carries no net electrical charge and is its point of minimum solubility. Isoelectric point determination is a well-known procedure which can be performed by any of several recognized methods (Yang and Lange, 1987). The optimal buffer solution should have a pH at least one pH unit away from the pI in order to avoid solubility problems. (I.e., if the particular plant leaf protein has a pI of 5.5, then the buffer solution should not have a pH between 4.5 and 6.5).

Based on the two factors above (plant leaf pH and protein pI), the researcher should then conduct an analysis to determine the optimal pH for the buffer solution. An example of such an analysis is the test described in FIG. 1 and supporting text. The pH levels of a given buffer solution can be adjusted using well known procedures by altering the ratio of the different components of the solution using procedures. The range of pH values to be tested should be those values which are within two pH units from the pH of the liquid leaf material but not within one pH unit from the pI of the leaf protein. So in the example above, if the pH of the leaf material were 7.0 and the pI of the leaf protein was 5.5, then the range of pH values to be tested would extend from pH 6.5 to pH 9.0.

The concentration of soluble protein in the extraction buffer solution can be assayed using the modified Bradford method (Bradford, 1976; Kruger, 1994). Application of this method should indicate a pH level which maximizes the solubility of the leaf proteins for a particular leaf protein.

Figure 1:
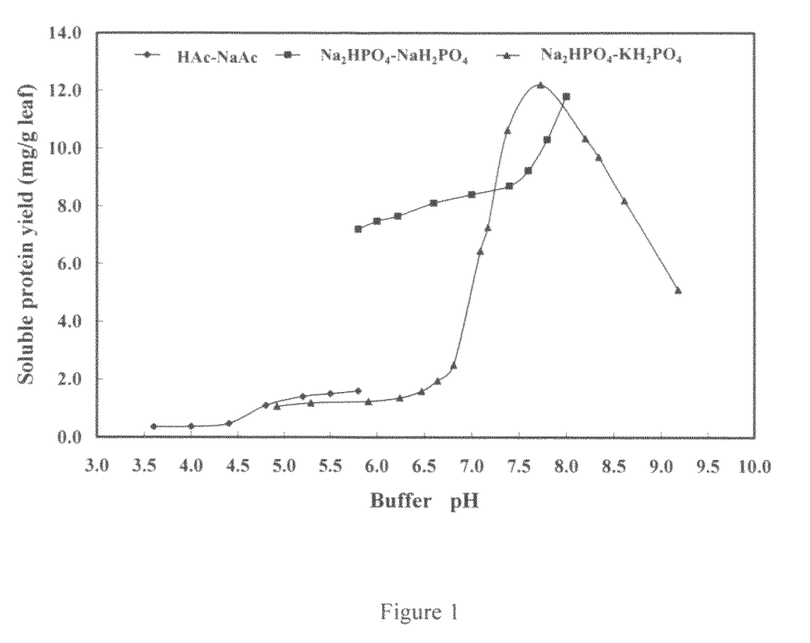
FIG. 1 shows the effect of buffer agents and pH on the tobacco soluble protein yield.

The user can conduct a soluble protein assay using these same or any known techniques, with any of the buffer solutions listed below or others as desired (for example as shown in FIG. 1 and described in the supporting text) to determine which buffer solution best (or at least adequately) promotes protein solubility. The buffer solution must be able to consume hydrogen and hydroxide ions and thereby resist changes in pH when small quantities of acids or bases are added to it. It is advisable to compare at least two different buffer solutions to determine which provides the best solubility. The buffer solutions selected for testing should be solutions which have a buffering region which overlaps with the range of pH levels to be tested. In the common scenario in which the pH range of interest is from 6.5 to 9.0, it would be worthwhile to compare at minimum $Na_2HPO_4$—$NaH_2PO_4$ and $Na_2HPO_4$—$KH_2PO_4$, as both buffer solutions have a buffering region in this pH range.

Another important test is the buffer concentration. It may happen that the peak soluble protein yields at the optimal pH levels are roughly similar for two different buffer solutions. (In fact, FIG. 1 illustrates such a situation). A buffer concentration test can then be performed at the optimal pH (as shown, for example, in FIG. 2 and described in the supporting text) to determine which buffer solution produces its optimal soluble protein yield at the lowest buffer concentration. The buffer solution which achieves optimal yield at lower buffer concentration is preferable, since it presents less risk of undesirable protein-salt interactions. There may also be cost savings associated with the lower concentration.

Figure 3:
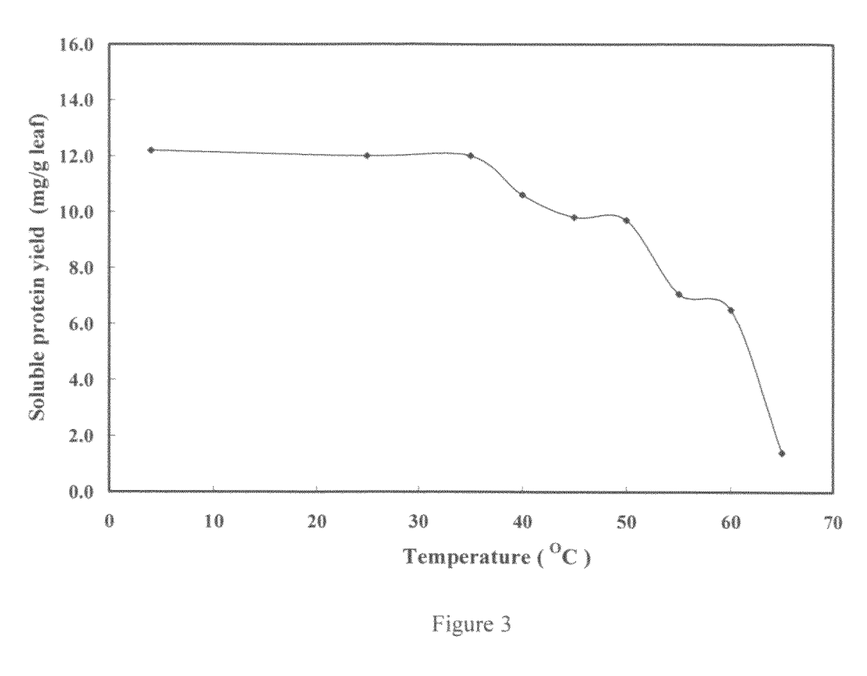
FIG. 3 shows the effect of incubation temperature on the tobacco soluble protein yield.

Another parameter (temperature) can be ascertained using the parameters and methods set forth, for example, in FIG. 3 and the supporting text. The range of temperatures tested for any given protein can extend from approximately 4° C. (refrigeration) up to as high as 55° C. As a practical matter, it is likely that any temperature above 40° C. will result in some protein denaturation, so the focus of tests should be in the lower portion of this range.

Figure 4:
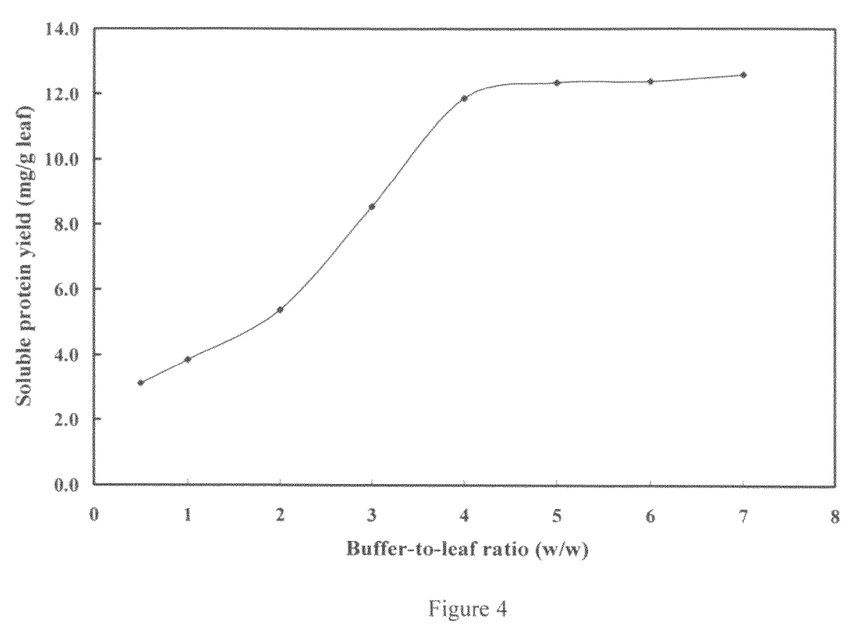
FIG. 4 shows the effect of buffer-to-leaf ratio on the tobacco soluble protein yield.

The user can determine the optimal buffer-to-leaf (BTL) ratio for promoting leaf protein solubility using the selected buffer solution and the procedures and methods, for example, as set forth in FIG. 4 and supporting text. The range of ratios to be tested should be between approximately 1:1 and approximately 8:1.

It is advisable to include both a chelating agent and a reducing agent in the buffer solution, for the reasons described in this disclosure. While any of the chelating and reducing agents listed herein may prove useful, EDTA and 2-mercaptoethanol, respectively, are commonly used in related application. We recommend ratios of approximately 37 grams of EDTA and 19.5 grams of 2-mercaptoethanol, respectively, per liter of water in preparing the buffer solution, based on our results described herein. Tap, distilled or deionized water is suitable for preparing the buffer solution.

The above procedures, which are very straightforward for one reasonably skilled in the art, will identify the suitable parameters of a buffer solution for use in recovering leaf proteins from any given species, including the composition of the solution, optimal pH level, buffer concentration, temperature and buffer-to-leaf ratio. The procedures for removing cellulosic material and chloroplasts described below in this disclosure (i.e., filtration, centrifuging, etc.), will be applicable for all useful plant species.

One plant that yielded good results using our method was tobacco. The inventors found that sodium phosphate dibasic/potassium phosphate monobasic was a preferred buffer system for tobacco. This combination proved effective to keep the proteins soluble and prevent denaturing. The inventors found that the pH of the preferred buffer solution should be between about 6.5 and about 9.0, more preferably between about 7.4 and about 8.0, and more preferably about 7.7. A pH below this range will result in a low yield of protein; a pH above this range will result in reduced yield and possible denaturation of the protein. The range of pH about 7.4-8.0 is preferred because this range is sufficiently close to the pH of the leaves but sufficiently far from the pI to maximize solubility while minimizing denaturation.

For all plants (not just tobacco), the concentration of the buffer solution should be within the range of about 0.025M to about 0.3M. (As someone having ordinary skill in this art would understand, molar concentration is represented by capital M and is calculated by moles per liter (M/L).) Concentrations below this range result in insufficient buffering effect; concentrations above this range result in salting out and possible salt-protein interaction that reduces protein purity, and also unnecessarily costly due to the high volumes of buffer used. The preferred concentration is between about 0.067M-about 0.2 M, and more preferably is approximately 0.067M.

In addition, and with regard to plants in general, the inventors found that the buffer-to-leaf (BTL) ratio should be sufficient to insure that the buffer solution maintains contact with all of the surface area of the disrupted leaf material, which will be greater than 1:1 (w/w). Ratios below this result in insufficient solubilization of protein into the solution; ratios above 8:1 will be unnecessarily costly and may result in hydrolysis of the proteins in subsequent processing steps. Applying this principle to tobacco, the inventors found that the preferred BTL ratio range is about 3:1-8:1, and more preferably about 4:1 (w/w).

For tobacco, the buffering solution must have a buffering region which is effective at solubilizing proteins in the pH range of 6.5 and 8.9. As someone having ordinary skill in this art would readily understand, any buffering solution which proves effective at solubilizing leaf proteins in this range can be used. Possible buffering solutions include the system combinations: sodium phosphate dibasic and potassium phosphate monobasic ($Na_2HPO_4$—$KH_2PO_4$), potassium phosphate monobasic/sodium hydroxide, sodium hydroxide/citric acid, acetic acid/ammonium acetate, potassium hydroxide/potassium phosphate monobasic, citric acid/disodium phosphate, potassium phosphate monobasic/potassium phosphate, dibasic, potassium acid phthalate/sodium hydroxide, potassium carbonate/potassium tetraborate/potassium hydroxide/disodium EDTA dihydrate, Giordano's buffer, sodium acetate trihydrate/sodium chloride, tris(hydroxymethyl)aminomethane (Tris), EDTA/Tris/Hcl, 2-amino-2-(hydroxymethyl)-1,3-propanediol/Tris, Tris/EDTA, ammonium chloride/ammonium hydroxide, HEPES/NaCl, imidazole, phosphate, N-morpholinopropane sulfonic acid (MOPS), N-tris(hydroxymethyl)methyl-2-aminoethane sulfonic acid ("TES"), triethanolamine, and N-tris(hydroxymethyl)-methyl-glycine ("Tricine"). These are contemplated for use with tobacco but could be appropriate for other plant species as well.

If it is desired that the leaf proteins be utilized for food or pharmaceutical purposes, then the buffer system selected should be suitable for such uses. The preferred buffer system consists of sodium phosphate dibasic and potassium phosphate monobasic ($Na_2HPO_4$—$KH_2PO_4$), which is suitable for food and pharmaceutical-grade use.

Another optional but preferred component of the buffer solution is a chelating agent. By "chelating agent" it is meant chemicals that combine with metal ions and remove them from their sphere of action, also called sequestrants. They are used in food manufacture to remove traces of metal ions which might otherwise cause foods to deteriorate and clinically to reduce absorption of a mineral, or to increase its excretion; e.g. citrates, tartrates, phosphates, and EDTA. The chelating agent must effectively remove loose ions and neutralize free radicals in the protein-containing buffer solution, which helps keep the desired proteins from denaturing. This enhances and purifies the end product and helps maximize protein yield. A chelating agent is preferably used in a ratio of approximately 25-50 grams per liter of buffering solution Known chelating agents can be used, such as EDTA, citrates, tartrates, phosphates, NaEDTA, EGTA, HEDTA, DTPA, NTA, calcium citrate, calcium diacetate, calcium hexametaphosphate, citric acid, gluconic acid, dipotassium phosphate, disodium phosphate, isopropyl citrate, monobasic calcium phosphate, monoisopropyl citrate, potassium citrate, sodium acid phosphate, sodium citrate, sodium gluconate, sodium hexametaphosphate, sodium metaphosphate, sodium phosphate, sodium pyrophosphate, sodium tripolyphosphate, stearyl citrate, tetra sodium pyrophosphate, calcium disodium ethylene diamine tetra-acetate, glucono delta-lactone, potassium gluconate and the like, and their analogs, homologs and derivatives. The preferred chelating agent is 10 mM EDTA.

Another optional but preferred component of the buffer solution is a reducing agent, which can inhibit possible oxidation of the soluble proteins. The reducing agent must be effective to keep plant liquids from browning during the protein recovery process, as browning gives an undesirable appearance. Also, the reducing agent must be able to prevent or at least minimize oxidation and denaturation of the proteins, which in turn maximizes final protein yield. A reducing agent is preferably used in a ratio of approximately 10-50 grams per liter of buffering solution Known reducing agents can be used, such as 2-mercaptoethanol, 2-mercaptoethylamine-HCL, sodium metabisulfite, cysteine-HCL, Ellman's reagent, BME, DTT, glutathione, cystein, Tris (2-carboxyethyl)phosphine hydrochloride, TCEP disulfide, n-ethylmaleimide, TCEP-HCL, ferrous ion, lithium aluminium hydride ($LiAlH_4$), nascent hydrogen, sodium amalgam, sodium borohydride ($NaBH_4$), stannous ion, sulfite compounds, hydrazine, zinc-mercury amalgam (Zn(Hg)), diisobutylaluminum hydride, lindlar catalyst, oxalic acid ($C_2H_2O_4$), dithioerythritol, thioglycolate, glutathione, cysteinem ascorbate and the like, and their analogs, homologs and derivatives or any other reducing agent which is suitable to prevent or reduce oxidation of soluble proteins. The preferred reducing agent is 2-mercaptoethanol.

For example, a particularly preferred buffer solution in tobacco would comprise, consist essentially of, or consist of the following components: $Na_2HPO_4$, $KH_2PO_4$, EDTA (e.g., 10 mM) and 2-mercaptoethanol (e.g. 25 mM). For instance, in one liter of water (deionized, distilled or tap water are all acceptable), there is the following:
1000 ml water
8.052 g $Na_2HPO_4$
0.911 g $KH_2PO_4$
37.2 g EDTA
19.53 g 2-mercaptoethanol
The preferred buffer concentration is 0.067M, and the preferred pH is 7.77.

With respect to its use to recover leaf proteins for any suitable plant leaves, in the first step of the method of recovering leaf proteins, another novel element is that the temperature of the cell wall disruption in the presence of the buffer solution is between about 0° and about 25° Celsius. This is important because application of heat treatment can result in denaturation of the proteins. It represents a novel difference from prior known leaf protein recovery methods because prior methods generally involved at least some heating step to separate and/or coagulate the leaf protein. The preferred temperature range is between about 4° and about 10° Celsius, and is most preferably 4° Celsius. Thus, throughout the first step, the leaf proteins remain soluble/solubilized in the buffer solution, and preferably little or no denaturization is occurring.

In a preferred embodiment of our invention, after the first step is carried out, the disrupted plant leaves are maintained in the buffer solution for up to twenty-four hours. It may even be longer, although the ultimate protein yield will be lower. Preferably, this occurs at ambient temperature or lower. Permitting the plant leaves to remain in the buffer solution will improve solubilization of the proteins and ultimately improve protein yield. In the more preferred embodiment, storage will not exceed five hours.

In a second step of the method of leaf protein recovery, substantially all cellulosic material is removed. By "cellulosic material" it is meant cellulose, hemicelluloses or lignin. By "substantially all" it is meant that at least 99% of the cellulosic material is removed The cellulosic material or fibrous material can be removed using known methods or standard industrial filtration procedures, by hand or mechanically, including use of a screw press, juicer, fiber filter, flypress, blender, mechanical presser, mechanical dewatering devices, and the like. It is important to remove the cellulosic material because this is an impurity which can adversely affect the texture of the final protein powder (make it more fibrous) and thereby reduce product quality. For certain uses, such as food uses, the failure to adequately remove cellulosic material could render the protein powder unusable. Throughout the second step, the leaf proteins remain soluble/solubilized in the buffer solution, and preferably little or no denaturization is occurring. After the cellulosic material is substantially removed, a "green juice" containing the solubilized proteins and chloroplasts remains.

In a third step of the method of leaf protein recovery, the majority of (and preferably substantially all) plant chloroplast material is removed from the "green juice". By "plant chloroplast material" it is meant the plant chloroplasts themselves and materials associated with them, except for leaf proteins. By "majority" it is meant at least 80% of the material, although it is strongly preferred to remove 95% or more of the chloroplasts. It is important to remove the plant chloroplast material because failure to so will leave an undesirable green tint to the proteins, which may render them less valuable or even unusable for many food and industrial applications. The chloroplasts are removed using the well-known technique of centrifuging (continuous or disk) or vacuum filtration. Centrifuging is the preferred embodiment. Centrifuging should be of sufficiently long duration and force to remove all or substantially all green color from the proteins. Centrifuging will also remove all or most of the buffering materials. Someone having ordinary skill in this art would easily determine the optimal specific centrifuging parameters for each sample, but as a rule it is preferable that centrifuging continue for at least 20 minutes at a force of at least 12,000 g. This results in an "amber juice" containing the soluble proteins in solution. Throughout the third step, the leaf proteins remain soluble/solubilized in the buffer solution, and preferably little or no denaturization is occurring.

In a fourth step, the protein-containing solution of the third step is dried down to produce a powder or cake or other dried form comprising a concentration of leaf proteins. This drying down may be performed through well-known industrial drying techniques such as spray drying, vacuum drying or freeze-drying. Spray drying is the preferred embodiment. This drying process produces a stable soluble leaf protein powder. Also present in the final product may be small quantities of nucleic acids, salts and bound pigments. Preferably, any other remaining plant product besides protein will not be in any substantial amount so as to interfere with the use of the leaf proteins. Preferably, the dried product will have a purity of at least 95% protein, and more preferably will have a purity of 98%. The total yield of protein powder is preferably about as high as approximately 13% of dry leaf matter. This is considerably higher than the protein yields of known methods. The advantages of the dried powder form are that it is a very useable and versatile form of the leaf proteins, readily adaptable for commercial use.

In another embodiment, as an alternative to drying the amber juice it is possible to remove nucleic acids and bound small molecules contained in the above-described powder— resulting in a purer protein product. Following removal of the chloroplast material, the next step is to conduct an isoelectric point precipition of the amber juice at a pH ranging ±0.5 from the isoelectric point of the proteins. The isoelectric point for tobacco leaf protein is pH 4.2, which means that the isoelectric point should be carried out in a range from 3.7 to 4.7, with the preferred pH being at approximately 4.2. As the isoelectric point is the point at which the proteins in the amber juice do not have either a positive or negative charge, it is the point at which they are most readily precipitated and separated from other constituents. While it is generally considered that isoelectric point precipitation irreversibly denatures the resulting protein, we have found that a brief precipitation (preferably under 15 minutes, although it may be possible to precipitate the proteins for up to 40 minutes before denaturation irreversibly occurs), followed by resuspension of the proteins in the originally used buffer solution at the originally used pH. (For tobacco, this would be the above-described $Na_2HPO_4$—$KH_2PO_4$ buffer solution, at pH 7.77.) Following resuspension in the buffer solution, the proteins can be dried down to produce a protein powder with many of the nucleic acids and bound small molecules removed. Preferably, the result is a leaf protein powder containing 97.5% purity. More preferably, the result is a powder of 99% purity.

Thus, to recover leaf protein in even higher purity, the first three steps are carried out as described above. Then, the protein-containing solution from the third step (removal of chloroplast materials) is further purified by the additional steps of conducting isoelectric point precipitation (in tobacco, at a pH of 3.7-4.7 (that is, 4.2 (±0.5)) on the liquid product to precipitate a product containing the desired leaf proteins. Then the precipitate is resuspended in the above-described buffer solution, preferably at a higher pH (such as about 7.7) to avoid denaturation. The resuspension liquid is dried down as described above to produce a powder or cake or other dried form comprising a concentration of leaf proteins (e.g., both fraction-1 and fraction-2) of even higher purity—that is, the final product is substantially free of very small molecules such as nucleic acids and chloroplasts.

In another embodiment, fraction-1 protein is recovered by itself. As noted above, fraction-1 protein contains large amounts of rubisco, which is considered of value. The first three steps are carried out as described above. Then, the liquid product resulting in the third step (removal of chloroplast materials) is further purified by the additional steps of conducting isoelectric point precipitation (in tobacco, at a pH of 5.3) on the liquid product to precipitate a product containing the desired fraction-1 leaf proteins. Any supernatant containing fraction-2 protein is then removed (e.g., by centrifugation and discard of the supernatant). The precipitate is resuspended in the above-described buffer solution, preferably at the original pH of the buffer solution (in tobacco, about 7.7) to avoid denaturation. The resuspension liquid is dried down as described above to produce a powder or cake or other dried form comprising a concentration of fraction-1 leaf proteins of good purity—that is, the final product is substantially free of fraction-2 protein, very small molecules such as nucleic acids and chloroplasts. Preferably, this fraction-1 product will have a purity of at least 90%, and more preferably will have a purity of at least 99%.

In another embodiment, fraction-2 protein is recovered by itself. The first three steps are carried out as described above. Then, the liquid product resulting in the third step (removal of chloroplast materials) is further purified by the additional steps of conducting isoelectric point precipitation (in tobacco, at a pH of 5.3) on the liquid product to precipitate a product containing fraction-1 leaf proteins. The supernatant containing fraction-2 protein is then collected (e.g., by centrifugation and discard of the precipitant). Another isoelectric point precipitation is conducted at a pH of 4.2, which will precipitate fraction-2 protein. The precipitate is resuspended in the above-described buffer solution, preferably at a higher pH (such as about 7.7) to avoid denaturation. The resuspension liquid is dried down as described above to produce a powder or cake or other dried form comprising a concentration of fraction-2 leaf proteins of good purity—that is, the final product is substantially free of fraction-1 protein, very small molecules such as nucleic acids and chlorplasts. Preferably, this fraction-2 product will have a purity of at least 90% %.

In a further embodiment in tobacco, purified rubisco crystals are recovered. In this method, the first three steps are carried out as described above. Then, with the liquid product resulting in the third step (removal of chloroplast materials) isoelectric point precipitation is conducted at a pH of about 5.3 to precipitate a product comprising fraction-1 protein and substantially no fraction-2 protein (e.g., using high centrifugation, for instance at 12,000 g for about 20 minutes), and a supernatant containing a clear portion. The clear portion of the supernatant is collected, to which ammonium sulfate, preferably solid, is added This liquid is then precipitated, and the precipitated material is removed. Ammonium sulfate, preferably solid, is added to the liquid remaining, and this solution is precipitated (e.g., by centrifuging), and the precipitated material is collected. The precipitated material is collected and resuspended in the buffer solution (preferably at a pH of about 7.7). Standard crystallization procedures are then carried out (usually including minimally dialyzing the solution, vaporizing the solution and cooling the solution). The resultant ribulose 1.5-bisphosphate carboxylase (rubisco) is then collected, and preferably washed. The rubisco crystals preferably are at least 90% pure, and more preferably at least 99% pure.

Further embodiments and variations within the scope of this invention are described in more detail below.

DETAILED DESCRIPTION OF THE INVENTION

Using the methods of this invention, the inventors have been able to obtain leaf protein recovery rates of approximately 13% of total leaf dry weight in tobacco. While already demonstrated to be useful in tobacco (*Nicotiana tabacum*), this technology is also readily adaptable to other plant species, including but not limited to other *Nicotiana* species, alfalfa and spinach, and tomato and potato. In fact, several researchers have demonstrated that techniques which are useful for recovering leaf proteins from tobacco are also useful for recovering leaf proteins from other species, such as other *Nicotiana* species, alfalfa and spinach (Bourque, 1982; Johal, 1982). As would be understood by someone having ordinary skill in this art, the methods of our invention are applicable for recovering leaf proteins from any plants containing soluble leaf proteins.

The invention represents a number of advantages over known methods, including the following non-exclusive list of advantages:

1. By maintaining the leaf proteins in solution throughout the process, we simplify the process of removing non-protein material.
2. We can conduct this procedure entirely under refrigeration or room temperature conditions. Many of the prior art practices required heating to separate the proteins, which can cause partial denaturing of the proteins.

3. It is possible to conduct the entire process using materials which are safe and suitable for production of leaf proteins for food products.
4. This process results in a leaf protein product in a soluble powder form readily for industrial use.
5. This process has resulted in protein yields superior to that obtained in the prior art.
6. The process for producing leaf protein powder products is very straightforward, with a minimum of steps. This simplification of the process makes it scalable to a bulk production. The prior art has focused the crystallization of rubisco, which has resulted in a series of technologies involving many complex steps which have not proven scalable to industrial production.

As noted above, the disclosed method is characterized by its simplicity and minimum number of steps needed—and its surprising high yield of good purity. The method entails at a minimum four steps: (1) disruption of cell walls to expose proteins in the presence of the buffer solution, at temperatures between about 0°-about 25° Celsius (which temperature is maintained throughout the process), under conditions such that the buffer solution contacts the plant leaves simultaneously with cell wall disruption, so as to contact the exposed leaf proteins as soon as possible; (2) removing cellulosic material, while the leaf proteins remain soluble in the buffer solution; (3) removing plant chloroplast material, while the leaf proteins remain soluble in the buffer solution; and (4) drying down the leaf proteins. If it is desired that the leaf proteins be further purified, isoelectric point precipitation(s) may be additionally carried out.

Application of the Method Using Tobacco

Here is an example of how the method may be carried out, using the example of tobacco. A subsequent discussion addresses how an individual reasonably skilled in the art may replicate this method using other species.

Freshly harvested green plant leaves are chopped with a hammermill. The leaves can be either freshly harvested, or they can be stored in a cool or frozen state or dried following harvest until they are ready for processing. Alternatively, physical maceration procedures, combined with mechanical pressure, can be utilized to disrupt the cell wall and prepare the proteins for solubilization (DeJong, 1982). It may also be possible to perform some of this leaf or cell disruption on-farm at the time of harvesting so that the proteins are solubilized into a liquid mixture at or just after the time of harvest, and this protein-containing liquid rather than the actual leaves are actually brought to the processing site. While some form of physical disruption of the leaves is essential in order to recover leaf proteins under this method, the invention is not dependent on any particular way of cell wall or leaf disruption.

The leaf protein recovery process should take place under refrigeration conditions (preferably approximately 4°-10° C.). While we have also successfully processed the leaf proteins at room temperature, maintaining refrigeration is preferred because it will minimize denaturation of the proteins. To that end, preparation of the buffer solution should also preferably take place at lower temperatures.

Substantially simultaneously with the leaf rupturing, a buffer solution is simultaneously added to the leaves. The inventors found that a solution containing sodium phosphate dibasic and potassium phosphate monobasic ($Na_2HPO_4$—$KH_2PO_4$) is especially effective, although other effective buffering agents are useful as described above. The inventors also found that a pH of 7.77 is preferable as it gave the highest protein yields with this agent, although a pH range between approximately 7.4-8.0 or even 6.5-9.0 is acceptable.

It is preferred that the buffer should have a low concentration, in order to avoid precipitating or denaturing the proteins. It was found that a buffer concentration of approximately 0.067M was the optimal concentration, although a range of 0.025M to about 0.3M is quite acceptable, and more preferably a range of about 0.067M-about 0.2 M.

It is preferred that the buffer solution should also contain both a chelating agent and a reducing agent. The purpose of the chelating agent is to remove loose ions from the resulting juice. We have found that 10 mM of EDTA, a well-known chelating agent, is effective to recover loose ions. The purpose of the reducing agent is to prevent oxidation and denaturation of the proteins. We have also found that 25 mM of 2-mercaptoethanol is effective as a reducing agent.

The ruptured leaves may be stored in the buffer solution for up to twenty-four hours, although preferably not more than five hours. While such storage is not necessary, it was found to help improve ultimate protein recovery.

An industrial filter may then be used to filter out the fibrous leaf biomass, leaving a green juice containing the soluble protein. We have found a screw press to give effective results.

This green juice contains the soluble proteins along with plant chloroplast materials. Subjecting this green juice to powerful centrifuge will remove this chloroplast material, leaving an "amber juice" which contains the soluble proteins. Centrifuging at a force of approximately 12,000 g for approximately 20 minutes is sufficient to remove leaf chloroplast materials. Either continuous centrifuge or disk centrifuge is suitable. However, failure to adequately centrifuge the green juice will result in incomplete removal of the chloroplasts, and can leave an undesirable green tint in the resulting proteins.

Figure 5:
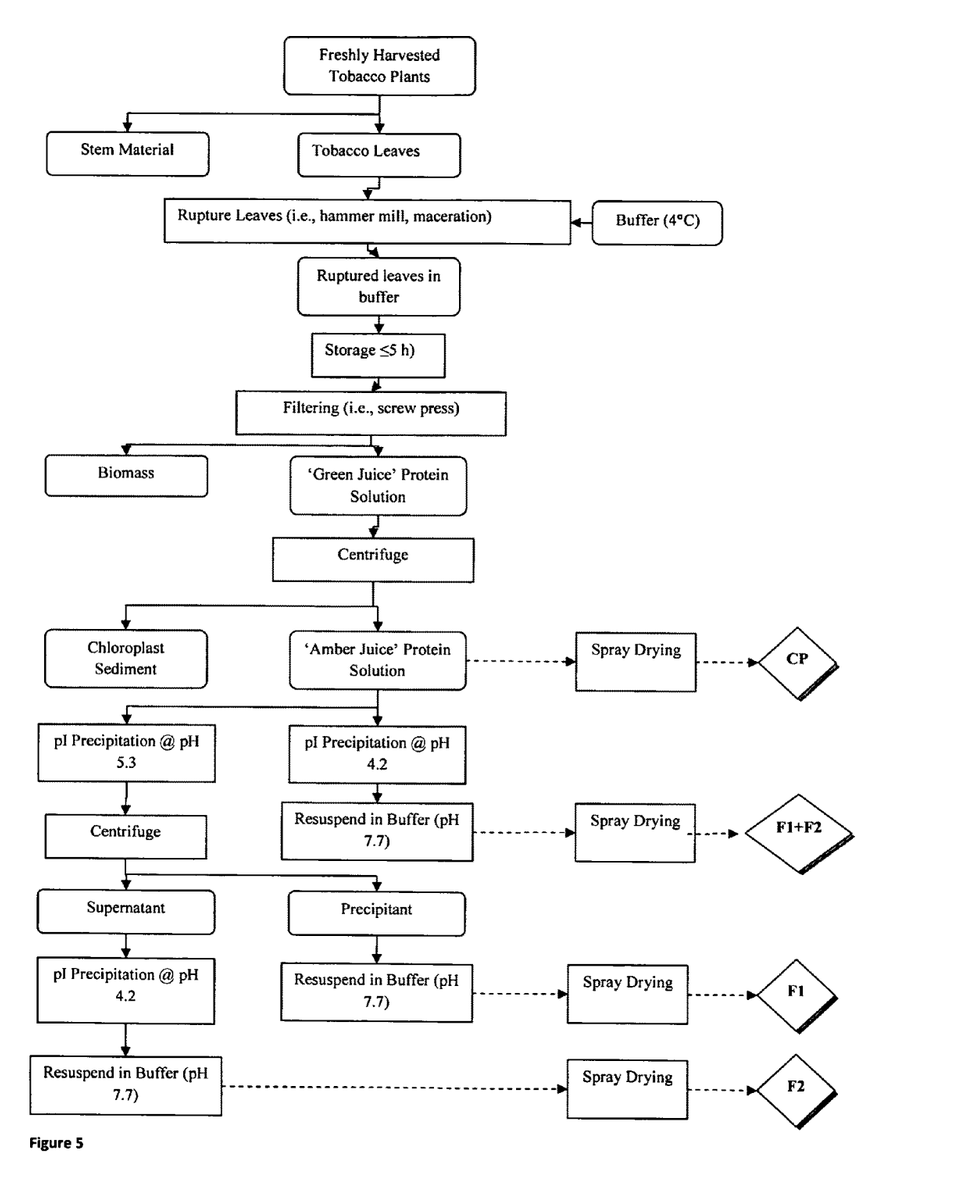
FIG. 5 is a flow chart illustrating the recovery process and potential alternative products.

Depending upon the desired use, it is possible to obtain several different protein products from this amber juice. The flow chart in FIG. 5 illustrates the recovery process and potential alternative products, and can be characterized as follows.

Product 1—Crude Protein Powder (CP on flow chart). The simplest approach is to prepare a protein powder product from this resulting amber juice through the use of standard industrial drying processes. This powder product can be prepared using spray drying, vacuum drying or freeze drying. However, spray drying is most practical for scale-up to an industrial level. This product will contain both fraction-1 and fraction-2 proteins, will be easily soluble in water and will have many of the same functional characteristics as are reported for pure rubisco. For example, we have found that this protein powder has superior binding characteristics to casein and soy protein when applied to a beta carotene pigment commonly used in food preparations, suggesting that this crude protein powder has excellent adhesive characteristics.

This crude protein powder could be satisfactory for many commercial uses. For example, it could prove useful as a protein coating product in paper (where its binding characteristics will help it fix colors) or in paints. However, this product contains impurities such as nucleic acid and bound small molecules.

Product 2—Purified Protein Powder. It is possible to remove these nucleic acids and small molecule impurities through a precipitation of the amber juice solution at its isoelectric point, which we have found to be at or about pH 5.3 (±0.5). The resulting solution can then be dried via spray drying or other industrial drying techniques to obtain a more highly purified powder product. This purified powder product contains both fraction-1 and fraction-2, is readily soluble, and possesses many of the same functional characteristics as rubisco.

Product 3—Separate Fraction-1 and Fraction-2 Powders. It is possible to separate the fraction-1 proteins from the fraction-2 proteins, and prepare separate products of each. Since the fraction-1 protein consists primarily of rubisco, this technique is particularly useful for applications in which a high concentration of rubisco is desirable, such as some medical applications. For example, it has been suggested that fraction-1 protein is an ideal nutrient source for dialysis patients and other persons whose bodies cannot produce adequate protein (Tornatzky, 1996). Using the amber juice described above, an isoelectric point precipitation was conducted at a pH of approximately 5.3 (±0.5), which is the isoelectric point for fraction-1 protein. This protein was then centrifuged at a force of approximately 12,000 g or greater. The precipitate was then resuspended in the above-described buffer solution at a pH of approximately 7.77. The precipitate was then dried using spray drying or other means to produce a powder product containing fraction-1 protein.

A powder product containing fraction-2 proteins can also be produced from the supernatant resulting from this centrifuge. An isoelectric point precipitation was additionally conducted involving the supernatant at a pH of approximately 4.2 (±0.5). The proteins were then resuspended in the buffer at a pH of approximately 7.77, and then dried using spray drying or other forms of drying.

Product 4—Highly Pure Rubisco Crystals—It is also possible to produce highly purified rubisco crystals starting from the amber juice. These crystals are suitable for use in scientific research. The amber juice was subjected to an isoelectric point precipitation at the isolectric point of rubisco, approximately pH 5.3 (±0.5), and then centrifuged at approximately 12000×g for approximately 20 min. The clear supernatant portion of this solution was then collected, and a small quantity of solid ammonium was added to the solution. The solution was then centrifuged and the precipitates of the resulting solution removed. A large quantity of solid ammonium sulfate was then added to the solution, followed by recentrifuging and collecting the insoluble precipitates of this solution. The buffer solution was then added at a pH of approximately 7.7 to resuspend the precipitates of the solution, following by dialyzing this solution, vaporizing this solution, and cooling this solution to crystallize ribulose 1.5-bisphosphate carboxylase/oxygenase. The crystals were then collected and washed. Applying this technique, we have obtained rubisco crystals of 99+% purity.

The invention is further described in the following non-limiting examples.

Experiments and Test Results

EXAMPLE 1

We performed an experiment to assess the effect of buffering agent and pH level on protein solubility. We tested three commonly used buffering agents:

0.2M HAc—NaCa buffer, at a pH range of 3.6 to 5.8 (HAc buffer)

0.2M $Na_2HPO_4$—$NaH_2PO_4$, at a pH range of 5.8 to 8.4 (sodium buffer)

0.067M $Na_2HPO_4$—$KH_2PO_4$ at a pH range of 4.9-9.2 (potassium buffer)

We found that the two sodium phosphate buffers were more effective at promoting protein solubility. We found that the sodium buffer yielded a maximum protein solubility of 2.46 mg/ml, at a pH of 8.33. We found that the potassium buffer yielded a maximum protein solubility of 2.43 mg/ml, at a pH of 7.77. We found that the HAc buffer gave much worse results, with a maximum protein solubility level of 0.31 mg/ml at a pH of 5.8. Most likely, the poor results of the HAc were due at least in part to the fact that the pH values tested were either close to the pI level of the protein (5.3) which minimized solubility, and the fact that the remaining values represented strongly acidic values. (See FIG. 1, "Effect of Buffering Solution and pH on Soluble Protein Yield").

EXAMPLE 2

In experiment 2, we tested five different buffer concentrations of both the sodium buffer and the potassium buffers, 0.05, 0.1, 0.15, 0.2 and 0.25 M, as follows:

$Na_2HO_4$—$NaH_2PO_4$ at pH 6.5

$Na_2HPO_4$—$KH_2PO_4$ at a pH of 7.77

We found that the potassium buffer had a much lower optimal buffer concentration than the sodium buffer. optimal buffer concentration for the potassium buffer was 0.067M. By contrast, the optimal buffer concentration for the sodium buffer, was 0.2M. Because the potassium buffer was effective at a substantially lower ionic concentration, we selected it as the optimal buffering agent. (See FIG. 2, "Effect of Buffer Concentration on Soluble Protein Yield").

EXAMPLE 3

Experiment 3 studied the effect of temperature on protein extraction. Using the sodium buffer, $Na_2HPO_4$—$NaH_2PO_4$, at pH 6.50, we found that lower temperature coincided with increased solubility. We found that an extraction process carried out at five temperatures between 15° C. and 60° C. We found that protein solubility was substantially higher when the process was performed at 15° C. than at any higher temperature. This result is significant and advantageous, since performing the extraction process at higher temperatures may cause denaturation of the proteins. (See FIG. 3: "Effect of Temperature on Soluble Protein Yield")

EXAMPLE 4

We tested several different buffer to leaf ratios to determine the optimal ratio for protein extraction, using the optimal parameters we had identified in earlier tests: the potassium buffer Na2HPO4-$KH_2PO_4$, at 0.067M concentration at pH 7.77. We tested several buffer ratios, ranging from 1:2 to 10:1 (buffer to leaf, on a fresh weight basis), comparing them in terms of protein yield. We found a 4:1 buffer to leaf ratio to be the optimal ratio. We found that a buffer to leaf ratio of 4:1 resulted in a protein yield of 958 mg/100 grams leaf. By contrast, a 3:1 buffer to leaf ratio resulted in a nearly ⅓ reduction of protein yield, to 654 mg per gram of leaf. Conversely, use of higher buffer to leaf ratios generated only marginally higher protein yields: a 6:1 ratio generated a protein yield of 962 mg protein/100 grams leaf while a 7:1 ratio generated 980 mg/protein/100 grams leaf. Given the added costs and water usage involved in using these higher buffer concentrations and the risk of downstream protein hydrolysis at high buffer levels, it is preferable to use a 4:1 ratio. (The dry weight concentration of tobacco leaves is approximately 8-10% of wet leaf weight.). (See FIG. 4, "Effect of Buffer to Leaf Ratio on Soluble Protein Yield").

EXAMPLE 5

Tobacco Leaf Protein Extraction Study

Tobacco (*Nicotiana tabacum* cv. MD-609LA) was grown on the University of Maryland Central Maryland Research and Education Center (Upper Marboro, Md.) during June- August of 2006 and 2007. Whole plants of tobacco were mechanistically harvested approximately 6 weeks after the transplant date, as indicated by the first appearance of a flower bud correspondent to tobacco plant physiological development that indicated the time for harvest. Each succeeding harvest after the first harvest occurred at ca. five week intervals following the first harvest. Freshly harvested plants were immediately misted with cool water, and transported within three hours to the UM Food Bioprocess Engineering Laboratory (College Park, Md.).

Upon arrival, the leaves of MD-609LA (500 g) were separated from the stalks, rinsed clean with tap water, macerated, and homogenized in a Waring Blender for 3 min with the buffer solution (details provided below) containing known volumes of 5 mM $Na_2EDTA$ (Fisher Scientific, Pittsburgh, Pa.) and 25 mM 2-mercaptoethanol (Sigma Aldrich, St. Louis, Mo.). HAc—NaAc, $Na_2HPO_4$—$NaH_2PO_4$, and $Na_2HPO_4$—$KH_2PO_4$ (respective effective buffering range at pH 3.6-5.8, 5.8-8.0, and 4.9-8.2) were investigated. The blended green tobacco slurry was stored at 4° C. for 12 hrs before filtered through 4 layers of cheesecloth to separate the biomass from the juice, which was subjected to centrifugation at 30,000×g for 20 min at 4° C. using a L7 ultracentrifuge (Beckman Coulter, Palo Alto, Calif.). The green sludge containing chloroplast, starch, and other particulate materials was then cheesecloth-filtered from the soluble protein solution, i.e., the supernatant. The amber-colored supernatants were collected and kept at 4° C. prior to further analysis. All extraction experiments were performed in triplicates.

Soluble Protein Assay

The concentration of soluble protein in the extraction buffer solution was assayed by the modified Bradford method (Bradford, 1976; Kruger, 1994), and the absorbance at 595 nm was measured in an Opsys Microtiter Plate Reader (Thermo Labsystems, Chantilly, Va.). All chemical reagents and lyophilized bovine serum albumin (BSA) used to construct the calibration curve were purchased from Bio-Rad Laboratories (Bio-Rad, Calif.).

Statistical Analysis

Experiments to optimize tobacco protein parameters were designed by response surface methodology (RSM) using the quadratic model in SPSS software (Ver. 10.0.5, SPSS Inc., Chicago, Ill.). The number of trials and the corresponding measurements were shown in Table 1. Data was presented as the means±standard deviation (SD) of three replicates, and Student's t-test was used to assess the significance of the data.

Buffer Selection and pH Adjustment

Release of protein from biological host is known to be highly dependent on the buffer system used and its corresponding pH values, since a proper buffer system could maintain pH stability of a solution (Haschemeyer, 1973; Bonner, 2007). Among the buffer systems investigated, the maximum soluble tobacco protein (up to 12.2 mg/g leaf) was achieved in $Na_2HPO_4$—$KH_2PO_4$ buffer at pH around 7.7, whereas $Na_2HPO_4$—$NaH_2PO_4$ buffer at pH 8.0 yielded 11.8 mg/g. The HAc—NaAc acidic buffer resulted in extremely low protein solubility (FIG. 1). The fact that tobacco protein tends to dissolve in a weak alkaline buffer system could be attributed to the isoelectric point (pI) of tobacco leaf protein which is 5.3.

Several studies have shown tobacco protein as a mixture of several proteins, including rubisco [>50% (w/w)] and rubisco activase, and their respective pI was at pH 5.9 and 5.1 (Komatsu et al, 1996; Nelson and Surzycki, 1976). Therefore, the effective pH range of alkaline buffer, namely pH 7.7 $Na_2HPO_4$—$KH_2PO_4$ and pH 8.0 $Na_2HPO_4$—$NaH_2PO_4$ employed in the present study, was located away from the pI of tobacco protein, consequently achieving the highest protein solubility. Furthermore, comparing with $Na_2HPO_4$—$NaH_2PO_4$ buffer (pH 8.0), $Na_2HPO_4$—$KH_2PO_4$ buffer at pH 7.7 was more suitable for extracting tobacco protein, since pH 7.7 was closer to the initial pH of tobacco leaves (pH 6.9) and could reduce denaturation and inactivation of protein during processing (Scopes, 1987). In addition, as seen in FIG. 1, the relatively low soluble protein yield of $Na_2HPO_4$—$KH_2PO_4$ buffer between pH 4.9 and 6.2 suggested that downstream purification of tobacco proteins could be achieved by pI aggregation of tobacco protein in $Na_2HPO_4$—$KH_2PO_4$ buffer at low pH.

Buffer Concentration

The concentration of buffer solutions was found to significantly impact the solubility of tobacco protein, more so in the $Na_2HPO_4$—$NaH_2PO_4$ system than in $Na_2HPO_4$—$KH_2PO_4$ (FIG. 2), with the latter showing higher solubility between the concentrations of 0.025 and 0.2 M. Such differences could be explained by the different ions-water interaction between $K^+$ and $Na^+$ (Fennema, 1996). In fact, it is well recognized that $K^+$ in dilute aqueous solution has a net structure-breaking effect, and results in a more fluid solution than pure water, which then promotes the trans-mass and dispersing efficiency between protein and water. The smaller positive ion, in this case $Na^+$, has strong electric fields influencing water molecular freedom, which results in decreasing the solution fluidity and lower protein solubility.

Figure 2:
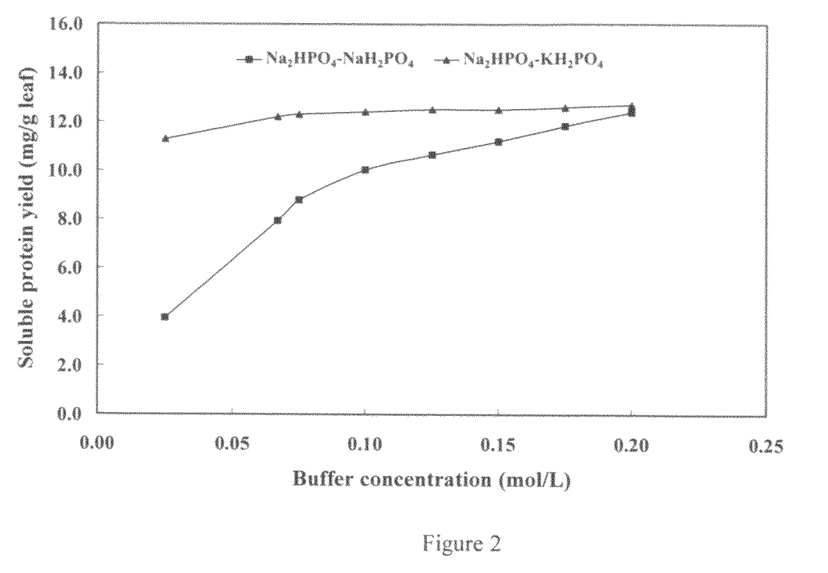
FIG. 2 shows the effect of buffer concentration on the tobacco soluble protein yield.

Equally noteworthy in FIG. 2 was that in both phosphate buffers the tobacco protein solubility increased with increasing buffer concentration, coincidental with the theory that a more concentrated buffer allows high buffering capacity in the working pH range of the buffer salt (Scopes, 1987). Nevertheless, at elevated salt concentrations, most salt ions are likely to be excluded from the protein's domain due to unfavorable interactions between the salt ions and the hydrophobic residues of the protein, which could easily result in salting-out behavior. Therefore, to enhance the yield of salt-free protein during subsequent treatments, the lowest possible concentration of $Na_2HPO_4$—$KH_2PO_4$ buffer showing stable protein solubility (ca. 12.1-12.3 mg/g of fresh leaf weight, or approximately 120 mg/g of dry leaf weight) between 0.067 and 0.2M was selected.

Effect of Incubation Temperature on Protein Extraction

Removal of chlorophyll bound to plant protein has conventionally involved an incubation period at around 47° C. (Fantozzi and Sensidoni, 1983; Tso and Kung, 1983). However, the influence of such high incubation temperature on the protein solubility and potentially denaturation remains unexamined. In the present study, the tobacco protein solution was incubated at different temperatures for 30 min before centrifugation at 4° C., and the effect of incubation temperature on the protein solubility was evident (FIG. 3)—as the incubation temperature increased, the solubility of protein was decreased.

As seen in FIG. 3, there were three distinct stages where soluble protein was reduced, namely around 35-45° C., 50-55° C., and above 60° C., with respective reduction of 19.67%, 44.67%, and 88.52%. Such reductions in protein solubility suggested that at these three temperature stages various degrees of protein denaturation occurred. As mentioned in the introduction, there are two major proteins in tobacco leaves: one is rubisco activase, whose unfolding and aggregation occurred at 37° C., and the other is rubisco that loses 50% total activity at 55° C. (Robinson et al, 1988; Salvucci and Anderson, 1987; Kim and Portis, 2006).

Therefore, the first two protein solubility reductions could be attributed to the denaturation of rubisco activase and rubisco, respectively. Moreover, it has been well recognized that most proteins and enzymes are thermally unstable above 60° C., as protein structure starts to unravel at such temperature (Haschemeyer, 1973). In most cool temperature conditions, the forces that hold a protein together, such as hydrogen bonding, ionic bridging, Van der Waals interactions, and hydrophobic interactions, are relatively weak but collectively the combination of these weak forces enables proteins to maintain their tertiary structure. These weak forces can be easily broken down by an increase in temperature above 60° C., which resulted in significant reduction in protein solubility, leaving only 11.48% soluble protein in the solution.

Effect of Buffer-to-Leaf Ratio (BLR) and Storage Condition

The effect of buffer-to-leaf ratio (BLR) ranging from 1:1 (w/w) to 7:1 (w/w) on the yield of soluble protein was characterized (FIG. 6). The amount of soluble protein recovered from the buffer system increased with increasing BLR, and the maximal yield was reached at BLR of 4:1 to 5:1 (w/w). Theoretically, further increases in buffer volume should decrease the viscosity of a solid-liquid system, and consequently more protein could be released from tobacco leaves into the buffer solution (Hatti-Kaul and Mattiasson, 2003). However, not only will employment of excessive buffer solutions by itself be cost-prohibitive, the resulting dilute solutions will also hinder the effectiveness of downstream recovery and purification processes. It is, therefore, advisable that a reasonable BLR should be chosen for practical applications.

Optimization of Protein Extracting Parameters

To optimize the parameters involved in protein extraction, a search algorithm based on randomly cast net to stepwise approach the defined optimum was employed using the quadratic factorial model. Extracted by $Na_2HPO_4$—$KH_2PO_4$ buffer, the protein extraction process is dependent on three key operating parameters, namely buffer concentration, buffer-to-leaf ratio (BLR), and the pH of buffer. Based on the design, their effects on tobacco protein solubility could be assessed using the 1-12 factorial experiments and 13-15 center experiments that estimated the standard error (Table 1).

TABLE 1

Factorial experimental design for optimization of tobacco protein yield parameters using the quadratic model of response surface methodology (RSM)

| Trail | Buffer concentration (mol/L) | Buffer-to-leaf ratio (w/w) | pH | Tobacco protein yield (mg/100 g leaf) |
|---|---|---|---|---|
| 1 | 0.050 | 4.0 | 7.7 | 798 |
| 2 | 0.050 | 5.0 | 7.7 | 868 |
| 3 | 0.084 | 4.0 | 7.7 | 825 |
| 4 | 0.084 | 5.0 | 7.7 | 1003 |
| 5 | 0.067 | 4.0 | 7.4 | 717 |
| 6 | 0.067 | 4.0 | 8.0 | 786 |
| 7 | 0.067 | 5.0 | 7.4 | 877 |
| 8 | 0.067 | 5.0 | 8.0 | 906 |
| 9 | 0.050 | 4.5 | 7.4 | 842 |
| 10 | 0.084 | 4.5 | 7.4 | 978 |
| 11 | 0.050 | 4.5 | 8.0 | 940 |
| 12 | 0.084 | 4.5 | 8.0 | 988 |
| 13 | 0.067 | 4.5 | 7.7 | 910 |
| 14 | 0.067 | 4.5 | 7.7 | 920 |
| 15 | 0.067 | 4.5 | 7.7 | 915 |

The significance of linear, crossproduct and quadratic of each parameter were indicated in Table 2.

TABLE 2

Analysis of variance for extraction variables as linear, quadratic terms and interactions on response variables Table 2: Tobacco soluble protein yield (mg/100 g leaf)

| Source | D.F.[a] | Sum of Squares | R-Square | F Value | Pr > F | Significance |
|---|---|---|---|---|---|---|
| Model | 14 | 90543 | 0.9972 | 200.40 | <.0001 | **[b] |
| Linear | 3 | 55117 | 0.6071 | 365.98 | <.0001 | ** |
| Quadratic | 3 | 30174 | 0.3323 | 200.36 | <.0001 | ** |
| Crossproduct | 3 | 5252 | 0.0587 | 34.87 | 0.0009 | *[c] |
| Lack of Fit | 3 | 201 | 67.000 | 2.68 | 0.2834 | |
| Pure Error | 2 | 50 | 25.000 | | | |

[a]D.F. is degree of freedom. B
[b]High significance at the 0.001 level.
[c]Significance at the 0.001 level.

The data of figures showed that the optimal operating parameters were found as the ratio of buffer to leaf was 4.75(w/w), pH 7.85 and buffer concentration about above 0.085M. These results were in great agreement with that data from above single factor experiments. Furthermore, the quadratic regression equation according to the SPSS parameter estimate of response surface was showed as follows:

$$Y = 915 + 43.25X_1 + 66X_2 + 25.75X_3 + 37X_1^2 + 27X_2X_1 - 78.5X_2^2 - 22X_1X_3 - 10X_2X_3 - 15X_3^2$$

Where Y is tobacco protein yield, $X_1$ represents buffer concentration, $X_2$ represents ration of buffer to leaf, and $X_3$ represents pH of buffer.

Regression Analysis of Response Surface is shown in Table 2. The results of variance test and significance test, indicated F values of linear, quadratic were highly significance, and crossproduct was significance as well. So the conclusion can be drawn that the changes of response are very complex, the relation between each factor and response values is not a simple linear function, but rather a quadratic function. Meanwhile, the values of lack of fit and pure error are very small, which indicated the fitness of the equation is good, and it can simulate the analysis of real experiment data.

The verifying experiment was carried out under the optimal conditions as mentioned above, the ratio of buffer to leaf was 4.75(w/w), pH 7.85 and buffer concentration 0.085 M, the tobacco soluble protein yield of 12.85 mg/g fresh leaf was achieved. We have consistently found that tobacco leaf dry weight is approximately 10% of the fresh weight. Therefore, our total soluble protein yield represented approximately 128.5 mg/g of the total leaf dry weight, or approximately 13%. Further, according to the data of total protein content 25.47 mg/g fresh leaf assayed by Kjeldahl method, the soluble tobacco protein with the optimal phosphate buffer system under controlled condition amounts up 50.45% of total protein in tobacco MD609LA leaf.

REFERENCES

Ginzel, K. H. (1992). Food from tobacco—A well-kept secret. *Priorities:* 4(1).
Pirie, N. W., "Leaf Protein and its by-products in human and animal nutrition." Cambridge University Press: Cambridge, U.K. pp. 15-16 (1987)
Pirie, N. W., "The Direct Use of Leaf Protein in Human Nutrition," *Chem. & Ind.* 61: 4-48, 1942.

Sheen, S. (1991). Comparison of chemical and functional properties of soluble leaf proteins from four plant species. *J. Agric. Food Chem.* 39: 681-685.

Tornatzky, L., Y. Batts, L. Casson, W. Loomis, and P. Waugaman (1996). *Prospects for Plant-Based Biotechnology Products.* The Southern Technology Council (STC).

Tso, T. C. (1990). Production, Physiology, and Biochemistry of Tobacco Plant, Ch. 22: Organic Metabolism—Tobacco Proteins." Ideals, Inc., Beltsville, Md.

Tso, T. C. (2006). Tobacco research and its relevance to science, medicine and industry. *Contributions to Tobacco Research.* 22: 133-146.

Wikipedia. Leaf Protein Concentrate.

Wildman, S. (1983). An Alternate Use for Tobacco Agriculture: Proteins for Food Plus a Safer Smoking Material.

Bonner, P. L. R., 2007. Groundwork. In: Bonner, P. L. R., Protein purification. Taylor & Francis Group, New York, N.Y., pp 26.

Bradford, M. M., 1976. A rapid and sensitive method for the quantitation of microgram quantities of protein utilizing the principle of protein dye binding. Anal. Biochem. 72, 248-254.

Degl'Innocenti, E., Guidi, L., Pardossi, A., Tognoni, F., 2005. Biochemical study of leaf browning in minimally processed leaves of lettuce (*Lactuca sativa* L. Var. Acephala). J. Agric. Food Chem. 53, 9980-9984.

Fantozzi, P., Sensidoni, A., 1983. Protein extraction from tobacco leaves: technological, nutritional and agronomical aspects. In Bodwell, C. E., Petit, L., Plant protein for human food. W. Junk Publishers., New York, N.Y., pp. 147-149.

Fennema, O. R., 1996. Water and ice. In: Fennema, O. R., Food Chemistry. Marcel Dekker, Inc. New York, N.Y., pp 32-33.

Haschemeyer, R. H., 1973. Fractionation and analysis of proteins. In: Haschemeyer, R. H., Proteins: a guide to study by physical and chemical methods. John Wiley & Sons Inc, New York, N.Y., pp 35.

Hatti-Kaul, R., Mattiasson, B., 2003. Release of protein from biological host. In: Hatti-Kaul, R., Mattiasson, B., Isolation and purification of proteins. Marcel Dekker, Inc. New York, N.Y., pp 1.

Henningfield, J. E., Benowitz, N. L., Slade, J., Houston, T. P., 1998. Reducing the addictiveness of cigarettes. Tob. Control. 7, 281-293.

Kim, K., Portis Jr., A. R., 2006. Kinetic analysis of the low inactivation of Rubisco during catalysis: effects of temperature, $O_2$ and $Mg^{++}$. Photosynth. Res. 87, 195-204.

Komatsu, S., Masuda, T., Hirano, H., 1996. Rice gibberellin-binding phosphoprotein structurally related to ribulose-1, 5-bisphosphate carboxylase/oxygenase activase. FEBS. Letters. 384, 167-171.

Kruger, N. J., 1994. The Bradford method for protein quantitation. In: Walker, J. M. (Ed.), Basic protein and peptide protocols. Humana Press Inc., Totowa, N.J., pp. 9-15.

Nelson, P. E., Surzycki S. J., 1976. A Mutant stain of chlamydomonas reinhardi exhibiting altered ribulosebisphosphate carboxylase. Eur. J. Biochem. 61, 465-474.

Platis, D., Labrou, N. E., 2006. Development of an aqueous two-phase partitioning system for fractionating therapeutic proteins from tobacco extract. J. Chrommatogy. A. 1128, 114-124.

Robinson, S. P., Streusand, V. J., Chatfield, J. M., Portis Jr., A. R., 1988. Purification and assay of Rubisco Activase from leaves. Plant. Physiol. 88, 1008-1014.

Salvucci, M., Anderson, J., 1987. Factors affecting the activation state and the level of total activity of Ribulose bisphosphate carboxylase in tobacco protoplasts. Plant. Physiol. 85, 66-71.

Scopes, R. K., 1987. Making an extract. In: Scopes, R. K., Protein purification principles and practice. Springer Verlag New York Inc, New York, N.Y., pp 26.

Simpson, R. J., 2004. Preparing proteins for proteomic analysis. In: Simpson, R. J., Purifying proteins for proteomics: a laboratory manual. Cold Harbor Laboratory Press, New York, N.Y., pp 17.

Tso, T. C., Kung, S. D., 1983. Soluble proteins in tobacco and their potential use. In: Telek, L.; Graham, H. D.; Leaf protein concentrates. AVI Publishing Company, Inc. Westport, Conn., pp 117-129.

Tso, T. C., 1990. Organic metabolism tobacco proteins. In Tso, T. C., Production, physiology, and biochemistry of tobacco plant. Ideals Inc., Beltsville, Md., pp. 487.

| U.S. Patent Documents | | |
|---|---|---|
| 4,588,691 | May 1986 | Johal |
| 4,400,471 | August 1983 | Johal |
| 4,340,676 | July 1982 | Bourque |
| 4,333,871 | June 1982 | DeJong |
| 4,334,024 | June 1982 | Johal |
| 4,268,632 | May 1981 | Wildman and Kwanyuen |
| 4,666,855 | May 1987 | Yang and Langer |
| 5,369,023 | November 1994 | Nakatani et al. |
| 7,034,128 | Apr. 25, 2006 | Turpen et al. |
| 4,347,324 | Aug. 31, 1982 | Wildman et al. |
| 4,289,147 | Sep. 15, 1981 | Wildman et al. |

What is claimed is:

1. A method for simultaneously recovering both ribulose-1,5-bisphosphate (RUBP) carboxylase/oxygenase ("rubisco") and non-rubisco soluble leaf proteins from plant leaves, which method is conducted throughout at a temperature between about 0°-about 25° Celsius, comprising the steps of:
   (a) simultaneously disrupting the cell walls of plant leaves and contacting rubisco and non-rubisco soluble proteins released from the disrupted plant leaves with a buffer solution, so that disrupted leaf materials and rubisco and non-rubisco soluble leaf proteins are exposed to the buffer solution and both the rubisco and non-rubisco soluble leaf proteins solubilize and are kept in the buffer solution,
   wherein the buffer solution (i) has a solute concentration between 0.025 M and 0.3 M; (ii) is present in a buffer-to-leaf ratio of greater than approximately 1:2 but not more than approximately 8:1; (iii) has a pH between 6.5 and 9.0; (iv) has a buffering region that is effective within the pH value of (iii); and (v) optionally comprises a chelating agent and/or a reducing agent;
   (b) removing from the buffer solution produced in step (a) substantially all cellulosic material to produce a buffer solution containing plant chloroplast material and the rubisco and non-rubisco soluble leaf proteins, which proteins remain solubilized therein,
   which step (b) occurs without adsorption on a solid support or removal by filtration of the rubisco or non-rubisco soluble leaf proteins;
   (c) removing from the buffer solution produced in step (b) at least 80% of the plant chloroplast material to produce a buffer solution containing the rubisco and non-rubisco soluble leaf proteins, which proteins remain solubilized therein, which step (c) occurs without adsorption on a solid support or removal by filtration of the rubisco or non-rubisco soluble leaf proteins;

wherein throughout steps (a), (b) and (c) both the rubisco and non-rubisco soluble leaf proteins remain solubilized and kept in the buffer solution while cellulosic material and plant chloroplast material are sequentially removed therefrom, and (d) drying down together in one product both the solubilized rubisco and non-rubisco soluble leaf proteins from the buffer solution, wherein said method further comprises steps between step (c) and step (d):

(aa) precipitating without denaturing soluble leaf proteins by conducting an isoelectric point precipitation on the buffer solution containing the solubilized leaf proteins, for up to 40 minutes at a pH of 5.3 equivalent to the isoelectric point of the soluble leaf proteins, or within .5 pH units of pH 5.3 of the isoelectric point;

(bb) removing any supernatant; and (cc) resuspending the precipitated soluble leaf proteins in the buffer solution.

2. The method of claim 1, wherein in step (a) the cell walls of the leaves are disrupted by chopping, milling, grinding or crushing the leaves, pulping, maceration procedures, mechanical pressure, rollers or homogenizing.

3. The method of claim 1, wherein after step (a) the soluble leaf proteins are maintained in the buffer solution for up to twenty-four hours.

4. The method of claim 3, wherein the soluble leaf proteins are maintained in the buffer solution at ambient temperature or lower.

5. The method of claim 1, wherein the buffer solution is a system suitable for protein extraction, selected from the group consisting of the combinations: sodium phosphate dibasic and potassium phosphate monobasic ($Na_2HPO_4$—$KH_2PO_4$), potassium phosphate monobasic/sodium hydroxide, sodium hydroxide/citric acid, acetic acid/ammonium acetate, potassium hydroxide/potassium phosphate monobasic, citric acid/disodium phosphate, potassium phosphate monobasic/potassium phosphate, dibasic, potassium acid phthalate/sodium hydroxide, potassium carbonate/potassium tetraborate/potassium hydroxide/disodium EDTA dihydrate, giordano's buffer, sodium acetate trihydrate/sodium chloride, tris(hydroxymethyl)aminomethane (Tris), EDTA/Tris/HC1, 2-amino-2-(hydroxymethyl)-1,3-propanediol/Tris, Tris/EDTA, ammonium chloride/ammonium hydroxide, HEPES/NaC1, imidazole, phosphate, N-morpholinopropane sulfonic acid (MOPS), N-tris(hydroxymethyl)methyl-2-aminoethane sulfonic acid ("TES"), triethanolamine, and N-tris(hydroxymethyl)-methyl-glycine ("Tricine").

6. The method of claim 1, wherein the chelating agent is selected from the group consisting of EDTA, EGTA, HEDTA, DTPA, NTA, calcium citrate, calcium diacetate, calcium hexametaphosphate, citric acid, gluconic acid, dipotassium phosphate, disodium phosphate, isopropyl citrate, monobasic calcium phosphate, monoisopropyl citrate, potassium citrate, sodium acid phosphate, sodium citrate, sodium gluconate, sodium hexametaphosphate, sodium metaphosphate, sodium phosphate, sodium pyrophosphate, sodium tripolyphosphate, stearyl citrate, tetra sodium pyrophosphate, calcium disodium ethylene diamine tetra-acetate, glucono delta-lactone, potassium gluconate and the like, and their analogs, homologs and derivatives.

7. The method of claim 1, wherein the reducing agent is selected from the group consisting of 2-mercaptoethanol, 2-mercaptoethylamine-HCL, cysteine-HCL, Ellman's reagent, BME, DTT, glutathione, cystein, Tris (2-carboxyethyl) phosphine hydrochloride, TCEP disulfide, n-ethylmaleimide, TCEP-HCL, ferrous ion, lithium aluminum hydride ($LiAlH_4$), nascent hydrogen, sodium amalgam, sodium borohydride ($NaBH_4$), stannous ion, sulfite compounds, hydrazine, zinc-mercury amalgam (Zn(Hg)), diisobutylaluminum hydride, lindlar catalyst, oxalic acid ($C_2H_2O_4$), dithioerythritol, thioglycolate, glutathione, cysteinem ascorbate, and their analogs, homologs and derivatives.

8. The method of claim 1, wherein in step (b) the cellulosic material is removed using a screw press, fly presser, blender, mechanical presser, mechanical dewatering device, or crusher.

9. The method of claim 1, wherein in step (c) the chloroplast material is removed using a centrifuge.

10. The method of claim 1, wherein in step (d) the drying down is done by spray drying, vacuum drying, or freeze drying.

11. The method of claim 1, wherein the plant leaves are from tobacco plants, plants of the species *Nicotiana*, alfalfa, ryegrass, tomato, spinach or potato.

12. The method of claim 11, wherein the plant leaves are from tobacco plants.

13. The method of claim 12, wherein the buffer solution comprises a buffer system of $Na_2HPO_4$ and $KH_2PO_4$ at a concentration of approximately 0.067 M, 10 mM EDTA, and 25 mM 2-mercaptoethanol, the buffer-to-leaf ratio is between 3:1 and 8:1, and the temperature is between approximately 4° and approximately 10° Celsius.

14. The method of claim 1, wherein the plant leaves are from tobacco plants, which comprises the further steps between step (c) and step (d):

precipitating soluble leaf proteins by conducting an isoelectric point precipitation on the buffer solution containing the solubilized leaf proteins, for up to 40 minutes at a pH between about 3.7 and about 4.7;

removing any supernatant; and resuspending the precipitated soluble proteins in the buffer solution.

15. The method of claim 1, wherein the plant leaves are from tobacco plants, which further comprises the steps between step (c) and step (d):

conducting isoelectric point precipitation for up to 40 minutes at a pH between about 3.7 and about 4.7 on buffer solution containing the solubilized leaf proteins to precipitate soluble proteins;

collecting supernatant;

conducting a second isoelectric point precipitation for up to 40 minutes at pH of about 4.2 on the supernatant to precipitate soluble proteins present therein; and resuspending the precipitated soluble proteins in the buffer solution and allowing the product to remain in resuspension.

16. The method of claim 1, wherein the total yield of Fraction 1 and Fraction 2 soluble leaf proteins in step (d) is 6% of the total leaf dry weight.

17. The method of claim 1, wherein the total yield of Fraction 1 and Fraction 2 soluble leaf proteins in step (d) is 8% of the total leaf dry weight.

18. A method for simultaneously recovering both ribulose-1,5-bisphosphate (RUBP) carboxylase/oxygenase ("rubisco") and non-rubisco soluble leaf proteins from plant leaves, which method is conducted throughout at a temperature between about 0° -about 25° Celsius, consisting of the steps:

(a) simultaneously disrupting the cell walls of plant leaves and contacting rubisco and non-rubisco soluble proteins released from the disrupted plant leaves with a buffer solution, so that disrupted leaf materials and rubisco and non-rubisco soluble leaf proteins are exposed to the buffer solution and both the rubisco and non-rubisco soluble leaf proteins solubilize and are kept in the buffer solution, wherein the buffer solution (i) has a solute concentration between 0.025 M and 0.3 M; (ii) is present in a buffer-to-leaf ratio of greater than approximately 1:2 but not more than approximately 8:1; (iii) has a pH between 6.5 and 9.0; (iv) has a buffering region that is effective within the pH value of (iii); and (v) optionally comprises a chelating agent and/or a reducing agent;

(b) removing from the buffer solution produced in step (a) substantially all cellulosic material to produce a buffer solution containing plant chloroplast material and the rubisco and non-rubisco soluble leaf proteins, which proteins remain solubilized therein, which step (b) occurs without adsorption on a solid support or removal by filtration of the rubisco or non-rubisco soluble leaf proteins;

(c) removing from the buffer solution produced in step (b) at least 80% of the plant chloroplast material to produce a buffer solution containing the rubisco and non-rubisco soluble leaf proteins, which proteins remain solubilized therein, which step (c) occurs without adsorption on a solid support or removal by filtration of the rubisco or non-rubisco soluble leaf proteins;

(d) precipitating the buffer solution produced in step (c) without denaturing soluble leaf proteins by conducting an isoelectric point precipitation on the buffer solution containing the solubilized leaf proteins, for up to 40 minutes at a pH of 5.3, or within .5 pH units of pH 5.3;

(e) removing any supernatant;

(f) resuspending the precipitated soluble leaf proteins in the buffer solution, wherein throughout steps (a)-(f) both the rubisco and non-rubisco soluble leaf proteins remain solubilized in the buffer solution, and (g) drying down both the solubilized rubisco and non-rubisco soluble leaf proteins from the buffer solution.

* * * * *